(12) United States Patent
Wymer et al.

(10) Patent No.: US 8,642,297 B2
(45) Date of Patent: Feb. 4, 2014

(54) PRODUCTION OF L-RIBOSE AND OTHER RARE SUGARS

(75) Inventors: Nathan Wymer, Ledyard, CT (US); Paul Taylor, Arlington Heights, IL (US)

(73) Assignee: ZuChem, Inc., Chicago, IL (US)

( * ) Notice: Subject to any disclaimer, the term of this patent is extended or adjusted under 35 U.S.C. 154(b) by 1630 days.

(21) Appl. No.: 11/501,997

(22) Filed: Aug. 10, 2006

(65) Prior Publication Data

US 2008/0227163 A1 Sep. 18, 2008

Related U.S. Application Data

(60) Provisional application No. 60/707,122, filed on Aug. 10, 2005.

(51) Int. Cl.
*C12P 17/04* (2006.01)
*C12N 1/21* (2006.01)
*C12N 1/19* (2006.01)

(52) U.S. Cl.
USPC ...................... 435/126; 435/252.3; 435/252.4

(58) Field of Classification Search
None
See application file for complete search history.

(56) References Cited

U.S. PATENT DOCUMENTS 3,669,845 A * 6/1972 Imai et al. ..................... 435/158
5,268,288 A 12/1993 Pharr et al.
6,348,326 B1 2/2002 Kawaguchi et al.

FOREIGN PATENT DOCUMENTS

WO  WO 03/095635 A2  11/2003
WO  WO 03/095635 A3  11/2003

OTHER PUBLICATIONS

Karabinos et al. Alditols by catalytic hydrogenation in Method of Carbohydrate chem.. 1963, Academic press p. 77-78).*
Simoni et al. PNAS, 1967, pp. 1963-1970.*
International Search Report for corresponding PCT application PCT/US2006/031283 dated Aug. 17, 2007.
Heuel, et al., "Genes for D-arabinitol and ribitol catabolism from *Klebsiella pneumoniae*", Microbiology, 144, 1631-1639 (1998).
Stoop, et al., "Purification of NAD-Dependent Mannitol Dehydrogenase from Celery Suspension Cultures", Plant. Physiol. 108:1219-1225 (1995).
Wolucka, et al., "GDP-Mannose 3',5'-Epimerase Forms GDP-L-gulose, a Putative Intermediate for the de Novo Biosynthesis of Vitamin C in Plants", The Journal of Biological Chemistry, vol. 278, No. 48, pp. 47483-47490 (2003).
Reiner, "Genes for Ribitol and D-Arabitol Catabolism in *Escherichia coli*: Their Loci in C Strains and Absence in K-12 and B Strains", Journal of Bacteriology, vol. 123, No. 2, pp. 530-536 (1975).
Yano, et al., "Directed evolution of an aspartate aminotransferase with new substrate specificities", Proc. Natl. Acad. Sci., vol. 95, pp. 5511-5515 (1998).
Schallmey, et al., "Developments in the use of *Bacillus* species for industrial production", Can. J. Microbiol., 50, 1-17 (2004).
Williamson, et al., "Sequence analysis of a mnnitol dehydrogenase cDNA from plants reveals a function for the pathogenesis-related protein ELI3", Proc. Natl. Acad. Sci., vol. 92, pp. 7148-7152 (1995).
Doong, et al., "Inhibition of the replication of hepatitis B virus in vitro by 2',3'-dideoxy-3'- thiacytidine and related analogues", Proc. Natl. Acad. Sci., USA, vol. 88, pp. 8495-8499 (1991).
Koeller, et al., "Emerging themes in medicinal glycoscinece", Nature Biotechnolgoy, vol. 18, pp. 835-841 (2000).
Ahmed, "Production of natural and rare pentoses using microorganisms and their enzymes", EJB Electronic Journal of Biotechnology ISSN, vol. 4, No. 2, pp. 103-111 (2001).
Allen, et al., "Pursuit of Optimal Carbohydrate-Based Anticancer Vaccines: Preparation of a Multiantigenic Unimolecular Glycopeptide Containing the Tn, MBr1, and Lewis$^y$ Antigens", J. Am. Chem. Soc., 123 p. 1890-1897 (2001).
Bartolozzi, et al., "New approaches to the chemical synthesis of bioactive oligosaccharides", Current Opinion in Structural Biology, 11(5):587-592 (2001).
Wang, et al., "Recent advances in L-nucleosides: chemistry and biology", Antiviral Research 40 (1998) 19-44.
Gumina, et al., "L-Nucleosides as chemotherapeutic agents", FEMS Microbiology Letters, 202 (2001) 9-15.
Du, et al., "A Practical Synthesis of L-FMAU from L-Arabinose", Nucleosides and Nucleotides, 18(2), 187-195 (1999).
Rouch, "Chiral Chemistry", Chemical and Engineering News, p. 45-61 (2004).
Jokela, et al., "Isomerization of pentose and hexose sugars by an enzyme reacter packed with cross-linked xylose isomerase crystals", Enzyme and Microbial Technology, 31 (2002) 67-76.
Seo, et al., "One-pot inversion of D-mannono-1,4-lactone for the practical synthesis of L-ribose", Tetrahedron Letters, 44 (2003) 3051-3052.
Bloom, et al., "Evolving strategies for enzyme engineering", Current Opinion in Structural Biology, 2005, 15:447-452.
Yang, et al., "Studies on the Substrate Specificity of *Escherichia coli* Galactokinase", Organic Letters, vol. 5, No. 13, 2223-2226 (2003).
Osepchuk, "A History of Microwave Heating Applications", IEEE Transactions on Microwave theory and Techniques, vol. MTT-32, No. 9, p, 1200-1224 (1984).
Nichols, et al., "Use of catabolite repression mutants for fermentation of sugar mixtures to ethanol", Appl. Microbiol. Biotechnol. (2001) 56:120-125.
Kroutil, et al., "Biocatalytic Oxidation of Primary and Secondary Alcohols", Adv. Synth. Catal., 2004, 346, 125-142.
Riebel, et al., "Cofactor Regeneration of both NAD$^+$ from NADH and NADP$^+$ from NADPH:NADH Oxidase from *Lactobacillus sanfranciscensis*", Adv. Synth. Catal., 2003, 345, 707-712.
Ödman, et al., "An enzymatic process to α-ketoglutarate from L-glutamate: the coupled system L-glutamate dehydrogenase/NADH oxidase", Tetrahedron: Asymmetry 15 (2004) 2933-2937.
Lee, "High cell-density culture of *Escherichia coli*", Trends in Biotech., 1996, 14, p. 98-105.
Reisenberg, et al., "High-cell-density cultivation of microorganisms", Appl. Microbiol. Biotechnol. (1999) 51:422-430.

(Continued)

*Primary Examiner* — Tekchand Saidha
*Assistant Examiner* — Md. Younus Meah
(74) *Attorney, Agent, or Firm* — McDonnell Boehnen Hulbert & Berghoff LLP

(57) ABSTRACT

The invention provides methods and compositions for the production of L-ribitol and other rare sugars using a mannitol-1-dehydrogenase.

23 Claims, 9 Drawing Sheets

(56) References Cited

OTHER PUBLICATIONS

Chang, et al., "High Density Cell Culture by Membrane-Based Cell Recycle", Biotech. Adv. vol. 12, pp. 467-487 (1994).

Zelder, et al., "Environmentally directed mutations and their impact on industrial biotransformation and fermentation processes", Current Opinion in Microbiology, 2000, 3:248-251.

Stoop, et al., "substrate Stereospecificity of the NAD-Dependent Mannitol Dehydrogenase from Celery", Phytochemistry, vol. 43, No. 6, pp. 1145-1150 (1996).

Bomati, et al., "Structural and Kinetic Basis for Substrate Selectivity in *Populus tremuloides* Sinapyl Alcohol Dehydrogenase", The Plant Cell, vol. 17, 1598-1611 (2005).

U.S. Appl. No. 60/707,122, filed Aug. 10, 2005.

* cited by examiner

PRODUCTION OF L-RIBOSE AND OTHER RARE SUGARS

PRIORITY

This application claims the benefit of U.S. Ser. No. 60/707,122, filed on Aug. 10, 2005, which is incorporated herein in its entirety.

GOVERNMENT INTERESTS

The government may have certain rights in the present invention pursuant to grant number 1R43AI065127-01 from the National Institutes of Health.

BACKGROUND OF THE INVENTION

Carbohydrates are playing an increasingly important part in biochemical research and in development of new pharmaceutical therapies, because carbohydrates are involved in a myriad of biological functions, including cellular recognition, signaling, and even the development of disease states. [1-4] Having access to consistent, pure and inexpensive carbohydrate starting materials is an important factor in the continuation of this research. This access is vitally important if the carbohydrate is not readily available from inexpensive sources, such as L-sugars and other rare sugars. Such sugars can only be used as starting materials for new biochemical and pharmaceutical compounds If their supply is not limited. The demand for the rare sugar L-ribose is increasing, because L-ribose is a starting material for many L-nucleoside-based pharmaceutical compounds. L-Nucleoside-based drugs have shown antiviral, antimalarial, and anticancer activities.[5] These nucleosides target many different viruses including HIV, hepatitis B (HBV), and Epstein-Barr.[6] The first nucleoside-based pharmaceutical therapy was (±)-2,3-dideoxy-3'-thiacytidine (BCH-189), displaying anti-HIV activity. To the surprise of many researchers, the L-form (L-3TC) was more potent and less toxic than the more "natural" D-form of BCH-189.[5] The interest in L-nucleosides has increased as noted in Table 1 showing several L-nucleoside-based pharmaceutical compounds presently in clinical trials. Many of these nucleoside-based drugs can be prepared from L-ribose, including Epivir, Elvucitabine, Clevudine, Telbivudine, and val-LdC.[7-9]

The need for inexpensive sources of L-ribose for the synthesis of L-nucleoside-based drugs is specifically seen in the synthesis of the nucleoside-based pharmaceutical drug 2'-deoxy-2'-fluoro-5-methyl-b-L-arabinofuranosyl uracil (L-FMAU). Chu and coworkers synthesized L-FMAU from L-arabinose.[10] However, their first synthetic step converted the L-arabinose to L-ribose. This step was needed because L-ribose is more expensive and less readily available than L-arabinose. By providing an inexpensive source of L-ribose, medicinal chemists can produce these and other drugs with fewer synthetic steps, decreased time, and increased yields that ultimately generate lower costs for researchers and patients.

The need for less expensive sources of L-ribose has become apparent from the dramatic increase in prices. A current bulk pricing for L-ribose is approximately $2500 per kg, up from the $700 to $1000 per kg seen quoted two years ago.[11] With the steady increase in anti-HIV and anti-HCV pharmaceutical candidates based on L-ribose currently undergoing clinical trials, prices for the L-ribose will surely continue to increase. Thus, dramatically increasing the costs of these life-saving drugs and pricing themselves out of reach for the HIV and HCV infected people in poor countries.

Currently, several companies are exploring synthetic routes for producing L-ribose. Each of these routes has their own limitations. Both Danisco and BioRefining produce L-ribose from L-arabinose extracted from natural sources, such as biomass, which requires extensive and expensive purification technologies.[12] The conversion of L-arabinose to L-ribose utilizes xylose isomerase.[13] This conversion is not very efficient, and therefore requires additional purification, further increasing costs.[13] HanChem uses a chemical process to convert D-mannose to L-ribose. This process uses a piperidine inversion of D-manno-1,4-lactone as the key synthetic step.[14] The second-generation process requires 8 synthetic steps and does not produce a high yield of L-ribose.[14] This route may become less commercially viable due to the increased cost of D-mannose.[11] Even if an inexpensive source of D-mannose were secured for this process, this eight-step synthesis would be too costly to create an inexpensive source of L-ribose. API has a fermentative route to L-ribose from D-glucose.[15] This route uses a Trichosporonoides strain, a Gluconobacter strain, and a Cellulomonas strain in separate fermentations to convert D-glucose to L-ribose.[15]

TABLE 1

Current L-nucleoside based pharmaceuticals currently approved by the United States Food and Drug Administration or undergoing clinical trials.

| Trade name | Generic Name | Company | Condition | Status (US) |
| --- | --- | --- | --- | --- |
| EPIVIR ® | 3TC (lamivudine) | GSK | HIV | approved |
| Elvucitabine | L-Fd4C (ACH-126,443) | Achillion | HIV, HBV | Phase II |
| Emtricitabine | FTC | Gilead | HIV, HBV | approved |
| Clevudine | L-FMAU | Bukwang | HBV | Phase III |
| Pentacept | L-3'-FD4C | Pharmasset | HBV | |
| Telbivudine | L-dT | Idenix Pharmaceuticals | HBV | Phase III |
| n/a | val-LdC | Idenix Pharmaceuticals | HBV | Phase IIb |
| troxacitabine | TROXATYL ®, BCH-4556 | BioChem Pharma Inc | solid tumors | Phase II |
| n/a | L-d4N | Idenix Pharmaceuticals | HBV | |

While D-glucose is an inexpensive starting material, the cost of the three-step sequential and separate fermentations is cost prohibitive.

SUMMARY OF THE INVENTION

These MDH systems can dramatically reduce the cost of producing L-ribose by utilizing a single fermentation step from ribitol, a readily available and inexpensive starting material. The production of L-ribose and other rare sugars described herein offers many advantages over the existing routes, namely using relatively inexpensive starting materials and a short and efficient synthetic route. None of the current commercial routes has all of these characteristics. By increasing the availability and lowering the cost of L-ribose and other rare sugars, biochemical and pharmaceutical researchers will have ready access a rare carbohydrates to produce better pharmaceutical therapies.

DETAILED DESCRIPTION OF THE INVENTION

This invention provides new synthetic routes to produce L-ribose and other rare sugars. These routes have advantages over the current synthetic strategies. The technologies developed for L-ribose production can then be translated into the production of other rare sugars to expand the portfolio of carbohydrate starting materials available to biochemists and synthetic carbohydrate chemists.

The production of L-ribose utilizes a NAD-dependent mannitol-1-dehydrogenase (MDH) from *Apium graveolens* (garden celery). *Apium graveolens* MDH specifically converts ribitol to L-ribose. MDH also has a broad substrate specificity profile that will allow the production of many different rare sugars from readily available and inexpensive polyols.

Active MDH has been expressed within *E. coli* and has been used to convert ribitol into L-ribose. Fermentation and bioconversion experiments have been performed with MDH to synthesize L-ribose and D-mannose. High-throughput assays have been developed for use in directed evolution experiments to improve the synthetic properties of MDH. These experiments successfully demonstrated the potential of a MDH system to synthesize L-ribose and also demonstrated flexibility in synthetic application. The synthetic potential of MDH can be improved with directed evolution and protein engineering to create a commercially viable and low-cost fermentation to synthesize L-ribose. MDH can also be used to produce larger quantities of other rare sugars that can be important for biochemical and medicinal chemistry research. The MDH system shows great potential in creating low-cost processes to synthesize a myriad of different rare sugars to aid in the development of more potent pharmaceuticals and decreasing the costs of synthesizing existing antiviral compounds.

A substrate of the invention can be substantially purified and can be present in a composition at a rate of 5%, 10%, 25%, 50%, 75%, 90%, 95%, 99%, or 100%.

A Unique Mannitol Dehydrogenase

Figure 1:
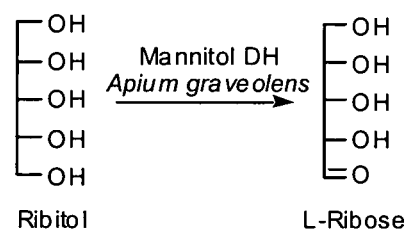
FIG. 1 shows the reaction of *A. graveolens* mannitol-1-dehydrogenase with ribitol.

Methods of the invention use a unique NAD-dependent mannitol dehydrogenase (MDH) from *A. graveolens*. [16-18] MDH is a unique mannitol dehydrogenase in that it is the only described mannitol-1-dehydrogenase (as opposed to the more common 2-mannitol dehydrogenase) and has been found to convert ribitol specifically to L-ribose.[16] See FIG. 1. This synthetic route is advantageous over the other commercial processes because it uses a readily available starting material in ribitol and only requires a single enzymatic transformation. The fermentation route to L-ribose can solve many of the problems associated with the other synthetic routes by using a single-step synthesis and an inexpensive starting material.

An *A. graveolens* MDH was originally identified, purified, and studied by Pharr and coworkers. [16-18] This MDH is unique in that it oxidizes D-mannitol to D-mannose instead of the usual D-mannitol to D-fructose transformation found with most mannitol dehydrogenases. BLAST searches of the *A. graveolens* MDH protein sequence shows that the MDH sequence is similar to other alcohol dehydrogenases, particularly various dehydrogenases from plants. In celery, mannitol serves as a phloem-translocated photoassimilate and is catabolized for entry into metabolism by the MDH.[17] Mannitol has also been shown to alleviate osmotic and salinity-induced stress in plants.[17] The novel specificity of MDH for the conversion of ribitol exclusively to L-ribose comes from the preference for an R-configuration of C2 of the resulting aldose.[16]

Polypeptides

A polypeptide of the invention can be post-translationally modified. A purified polypeptide (e.g., MDH, NADH oxidase, rbT protein) is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure.

Purified polypeptides of the invention can either be full-length polypeptides or fragments of polypeptides. For example, fragments of polypeptides of the invention can comprise about 50, 100, 250, 300, or 350 contiguous amino acids or more of polypeptides of the invention. Examples of a polypeptide of the invention include that shown in SEQ ID NO:2. Variant polypeptides are at least about 80, or about 90, 96, 98, or 99% identical to the polypeptide sequence shown in SEQ ID NO:2 and are also polypeptides of the invention. Variant polypeptides have one or more conservative amino acid variations or other minor modifications and retain biological activity, i.e., are biologically functional equivalents. A biologically active equivalent has substantially equivalent function when compared to the corresponding wild-type polypeptide.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variants can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g. has 90-110% of the activity of the original polypeptide.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature. Additionally, a polypeptide can be covalently or non-covalently linked to compounds or molecules other than amino acids. For example, a polypeptide can be linked to an indicator reagent, an amino acid spacer, an amino acid linker, a signal sequence, a stop transfer sequence, a transmembrane domain, a protein purification ligand, or a combination thereof. In one embodiment of the invention a protein purification ligand can be one or more C amino acid residues at, for example, the amino terminus or carboxy terminus of a polypeptide of the invention. An amino acid spacer is a sequence of amino acids that are not usually associated with a polypeptide of the invention in nature. An amino acid spacer can comprise about 1, 5, 10, 20, 100, or 1,000 amino acids.

If desired, a polypeptide can be a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and staphylococcal protein A, or combinations thereof. More than one polypeptide of the invention can be present in a fusion protein. Fragments of polypeptides of the invention can be present in a fusion protein of the invention. A fusion protein of the invention can comprise one or more of a polypeptide shown in SEQ ID NO:2, fragments thereof, or combinations thereof.

Polypeptides of the invention can be in a multimeric form. That is, a polypeptide can comprise one or more copies of SEQ ID NO:2. A multimeric polypeptide can be a multiple antigen peptide (MAP). See e.g., Tam, J. Immunol. Methods, 196:17-32 (1996).

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from *A. graveolens* cells.

Polynucleotides

Polynucleotides of the invention contain less than an entire genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. The polynucleotides of the invention encode the polypeptides described above. In one embodiment of the invention the polynucleotides encode a polypeptide shown in SEQ ID NO:2. Polynucleotides of the invention include those shown in SEQ ID NO:1, other polynucleotides encoding MDH, NADH oxidases, rbT proteins or combinations thereof. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and staphylococcal protein A.

Polynucleotides of the invention can be isolated. An isolated polynucleotide is a polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. A nucleic acid molecule existing among hundreds to millions of other nucleic acid molecules within, for example, cDNA or genomic libraries, or gel slices containing a genomic DNA restriction digest are not to be considered an isolated polynucleotide.

Polynucleotides of the invention can also comprise fragments that encode immunogenic polypeptides. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 90, 96, 98, or 99% identical to the polynucleotide sequences of the invention and the complements thereof are also polynucleotides of the invention. Percent sequence identity can be calculated as described in the "Polypeptides" section. Degenerate nucleotide sequences are polynucleotides that encode a polypeptide of the invention or fragments thereof, but differ in nucleic acid sequence from the wild-type polynucleotide sequence, due to the degeneracy of the genetic code. Complementary DNA (cDNA) molecules, species homologs, and variants of *A. graveolens* polynucleotides that encode biologically functional *A. graveolens* polypeptides also are *A. graveolens* polynucleotides. Polynucleotides of the invention can be isolated from nucleic acid sequences present in, for example, *A. graveolens* cell cultures. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to or close to one or more expression control elements, which direct transcription and/or translation of the polynucleotide.

Alternative Starting Materials for L-Ribose

While ribitol is a relatively inexpensive starting material, the process for L-ribose production could also start from D-ribose. D-Ribose is used in pharmaceuticals, cosmetics, health food, animal feed, and as a flavor enhancer in food.[19] World-wide fermentation production of D-ribose is approximately 2000 metric tons per year.[19] For the production of L-ribose, the D-ribose would be converted to ribitol by chemical reduction, such as hydrogenation, and then used for the fermentation process. A two-step enzymatic route could also be constructed for a single fermentation to convert D-ribose directly into L-ribose. D-ribose could be converted into ribitol by a reductase. This enzymatic route could be advantageous because no cofactor recycling would be needed. These alternative routes provide flexibility in creating the most economical production system to reduce the costs of L-ribose.

Production of Other Rare Sugars

Technology for L-ribose production will serve as an enabling model technology for the production of other rare sugars. MDH converts many different inexpensive polyols to rare sugars as shown in Table 2.

TABLE 2

Current prices (2005) of MDH synthetic targets as listed in the Sigma-Aldrich catalog of fine chemicals. The largest quantities available in the catalog are listed.

| Substrate | Price | Scale | Scaled Price Price/100 g | Product | Price | Scale | Scaled Price Price/100 g |
|---|---|---|---|---|---|---|---|
| i-Ribitol | $178 | 100 g | $178 | L-Ribose | $840 | 5 g | $16,800 |
| D-Mannitol | $142 | 5 kg | $3 | D-Mannose | $261 | 500 g | $52 |
| i-Galactitol | $79 | 100 g | $79 | L-Galactose | $867 | 1 g | $86,700 |
| D-Sorbitol | $40 | 3 kg | $1 | L-Gulose | $68 | 25 mg | $272,000 |
| D-Arabitol | $787 | 250 g | $315 | D-Lyxose | $23 | 5 g | $460 |
| i-Erythritol | $154 | 100 g | $154 | L-Erythrose | $127 | 100 mg | $127,000 |
| D-Threitol | $308 | 5 g | $6,160 | D-Threose | $62 | 50 mg | $124,000 |
| Potential Targets | | | | | | | |
| i-Xylitol | $83 | 1 kg | $8 | L-Xylose | $38 | 5 g | $760 |
| L-Arabitol | $284 | 100 g | $284 | L-Arabinose | $441 | 500 g | $88 |

All of these compounds are, or potentially could be, used in biochemical or pharmaceutical applications.[1, 4, 11] MDH could also be engineered to accept other substrates. For example, wild-type MDH does not convert xylitol to L-xylose, despite the correct R-configuration of C2 of the L-xylose. Using directed evolution, this specificity could be engineered into MDH.

The production of D-mannose from D-mannitol is particularly attractive since fermentation processes for D-mannitol from D-fructose are also needed. D-Mannose is currently used in the production of pharmaceutical agents, antibiotics as well as a homeopathic treatment for urinary tract infections.[1, 20] Currently, D-mannose is extracted from biomass, such as birch and beech tree pulp, thus requiring expensive purification technologies.[12] Engineered MDH could either use the purified mannitol from this process or the mdh gene could be expressed directly from the mannitol production strain. Using the two enzymes creates a direct route from D-fructose to D-mannose. Either route would significantly reduce the costs and increase availability of D-mannose for the research and pharmaceutical communities.

One embodiment of the invention provides a method of generating a variant of a nucleic acid encoding a polypeptide with a mannitol-1-dehydrogenase activity. The method comprises:
  (a) providing a template nucleic acid encoding an MDH;
  (b) modifying, deleting or adding one or more nucleotides in the template sequence, or a combination thereof, to generate a variant of the template nucleic acid;
  (c) expressing the variant nucleic acid to generate a variant MDH polypeptide.

The modifications, additions or deletions can be introduced to the template by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation or a combination thereof.

The significant potential of MDH systems was revealed in the following experiments for the large-scale commercial production of L-ribose and other rare sugars.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Expression of Mannitol-1-dehydrogenase

The goal of this experiment was to express active MDH in *E. coli* and test this activity for the production of L-ribose from ribitol. The sequence of MDH is shown in SEQ ID NO:2. An MDH gene was synthetically constructed for expression *E. coli*. Specifically, the primary DNA sequence of the gene was optimized for codon usage and the removal of potentially hindering secondary structure of the RNA coding sequence. See, SEQ ID NO:1. This gene was cloned into a pTTQ18 expression plasmid, a pUC-based plasmid containing an inducible tac promoter. The *E. coli* BL21 strain was then used for expression of SEQ ID NO:1. Software packages, such as, GeneOptimizer® are available that can provide sequences having optimized codon usage and hindering secondary structure removed.

```
                                            SEQ ID NO: 1
ATGGCGAAAAGCAGCGAAATCGAACACCCGGTGAAAGCGTTTGGTTGGG

CGGCACGTGATACCACCGGTCTGCTGAGCCCGTTCAAATTTAGCCGTCG

CGCGACCGGCGAAAAAGATGTGCGCCTGAAAGTGCTGTTTAGCGGCGTG

TGCCACAGCGATCACCACATGATCCACAACAACTGGGGCTTCACCACCT

ATCCGATCGTGCCGGGCCATGAAATTGTGGGCGTGGTGACCGAAGTGGG

CAGCAAAGTGGAAAAAGTGAAAGTGGGCGATAACGTGGGCATTGGCTGC

CTGGTTGGTAGCTGCCGTAGCTGCGAAAGCTGCTGCGATAACCGCGAAA

GCCACTGCGAAAACATCATCGATACCTACGGCAGCATCTACTTCGATGG

CACCATGACCCATGGCGGCTACAGCGATACCATGGTGGCGGATGAACAC

TTCATTCTGCGCTGGCCGAAAAACCTGCCGCTGGATTCTGGTGCACCGC

TGCTGTGTGCGGGCATTACCACCTACAGCCCGCTGAAATACTACGGCCT

GGATAAACCGGGCACCAAAATCGGTGTGGTGGGCCTGGGTGGTCTGGGT

CATGTGGCGGTGAAAATGGCGAAAGCGTTCGGTGCGCAGGTGACCGTGA

TCGATATCAGCGAAAGCAAACGCAAAGAAGCGCTGGAAAAACTGGGCGC

GGATAGCTTCCTGCTGAACAGCGATCAAGAACAGATGAAAGGCGCGCGT

AGCAGCCTGGATGGCATTATCGATACCGTGCCGGTGAATCATCCGCTGG

CGCCGCTGTTCGATCTGCTGAAACCGAACGGCAAACTGGTGATGGTTGG

TGCGCCGGAAAAACCGTTCGAACTGCCGGTGTTCAGCCTGCTGAAAGGC

CGTAAACTGCTGGGCGGCACCATTAACGGCGGCATCAAAGAAACCCAGG

AAATGCTGGATTTCGCGGCGAAACACAACATCACCGCGGATGTGGAAGT

GATCCCGATGGATTACGTGAACACCGCGATGGAACGCCTGGTGAAAAGC

GATGTGCGCTACCGCTTCGTGATTGATATCGCGAATACGATGCGTACCG

AAGAAAGCCTGGGCGCGTAA
```

-continued

```
                                             SEQ ID NO: 2
  1 MAKSSEIEHP VKAFGWAARD TTGLLSPFKF SRRATGEKDV
    RLKVLFXGVC HSDHHMIHNN

61 WGFTTYPIVP GHEIVGVVTE VGSKVEKVKV GDNVGIGCLV
    GSCRSCESCC DNRESHCENX

121 IDTYGSIYFD GTMTHGGYSD TMVADEHFIL RWPKNLPLDS
    GAPLLCAGIT TYSPLKYYGL

181 DKPGTKIGVV GLGGLGHVAV KMAKAFGAQV TVIDISESKR
    KEALEKLGAD SFLLNSDQEQ

241 MKGARSSLDG IIDTVPVNHP LAPLFDLLKP NGKLVMVGAP
    EKPFELPVFS LLKGRKLLGG

301 TINGGIKETQ EMLDFAAKHN ITADVEVIPM DYVNTAMERL
    VKSDVRYRFV IDIANTMRTE

361 ESLGA
```

SEQ ID NO:2 shows a MDH. In one embodiment the X at position 47 is S or C. In one embodiment of the invention the X at position 120 is I or T. In one embodiment of the invention the amino acids at positions 75-91 and/or the amino acids at positions 188-196 are highly conserved.

Many different variables were studied to maximize the expression and activity of MDH. MDH activity was monitored with the conversion of D-mannitol to D-mannose in the presence of NAD. The conversion was monitored spectrophotometrically by measuring the increasing concentration of NADH, the cofactor product of the oxidation of mannitol to mannose. For a given experiment, lysate protein concentrations were normalized.

Expression temperature, varying reducing agent concentrations, and the addition of varying types and concentrations of detergent were all investigated. An expression temperature of 30° C. appears to be optimal for wild-type MDH. Expressing recombinant MDH at 37° C. resulted in an eight-fold reduction in MDH activity. Reducing the expression temperature further to 16° C. resulted in almost no MDH activity. Dithiothreitol (DTT) and several different surfactants were added to the lysis buffer. Including 0.5% tween 80 and 1 mM DTT resulted in nearly a three-fold increase in MDH activity recovered.

Figure 2:
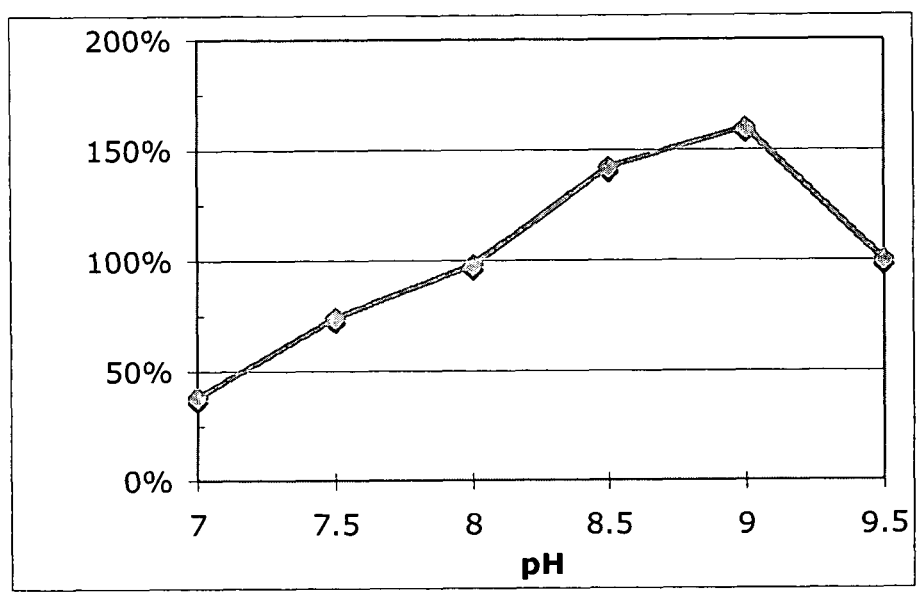
FIG. 2 shows activity vs. pH profile of MDH with D-mannitol. The rate was relative to pH 9.5.

The pH profile for MDH for the oxidation reactions was also tested. MDH showed the highest activity at pH 9.0. See FIG. 2. MDH showed decreased activity at a neutral pH range. This range could be beneficial for in vitro bioconversions with enzymatic NAD cofactor recycling methods. Increasing the activity of MDH at neutral pH could improve in vivo fermentation activity as the interior of the E. coli cell has a pH lower than 9.0.[21]

Substrate specificity of the recombinant MDH was also tested and compared with the published data on the natively expressed MDH. Recombinant expression of MDH in E. coli could cause subtle modifications to the tertiary structure of MDH and modify the substrate specificity. Several known substrates of the MDH were tested.[16]

TABLE 3

Relative reaction rates of various substrates when MDH is expressed natively or recombinantly.

| Substrate | Product | Recombinant MDH | Native MDH |
|---|---|---|---|
| D-Mannitol | D-Mannose | 100% | 100% |
| D-Arabitol | D-Arabinose | 33% | 37% |
| Erythritol | L-Erythrose | 4% | 16% |
| Ribitol | L-Ribose | 50% | 36% |
| D-Sorbitol | L-Gulose | 5% | 22% |
| Xylitol | L-Xylose | 1% | 0% |

Recombinantly expressed MDH showed a similar substrate specificity to natively expressed MDH. Table 3 illustrates the synthetic potential of an MDH system to produce a broad range of rare sugars from inexpensive and readily available starting materials.

MDH expressed well enough to show the significant potential of this system for the large-scale production of L-ribose and many different rare sugars. By using well-engineered screens and selection assays together with targeted random mutagenesis, directed evolution can be used to increase expression and activity of MDH. More purification schemes can also be used to simplify the purification of large quantities of MDH for use in the bioconversion of many different rare sugars.

While MDH can be expressed in E. coli and other bacteria, it can also be expressed in other hosts, such as yeast, including, e.g., Saccharomyces cerevisiae.

Example 2

Metal Requirements Including Inhibition

While not explicitly described in the literature[37-39], Apium gravelons mannitol-1-dehydrogenase (MDH) requires divalent metal ions, particularly $Zn^{2+}$ ions, for activity. The presence of $ZnSO_4$ increases MDH activity. Cells expressing MDH were grown in rich media were harvested and lysed with BUGBUSTER® protein extraction reagent, Novagen, Madison, Wis. MDH activity was then tested with increasing concentrations of $ZnSO_4$ in the presence of D-mannitol and NAD cofactor at pH 9.0. See, FIG. 1.

MDH activity showed a 50% increase with the addition of 1 µM $Zn^{2+}$ ions compared to no added zinc. Concentrations above 1 µM showed inhibition. High concentrations of other divalent metals are also inhibitory. The addition of 0.1 mM $NiSO_4$ also inhibits MDH activity approximately 50% compared to MDH without $NiSO_4$ added.

The metal requirement of MDH can also be seen in the growth media preparation for a fermentation bioconversion. Defined growth media such as M9 media without added trace metals do not generate MDH activity to convert ribitol to L-ribose. The same strain will catalyze this reaction when the cells are grown in rich media, such as Lauria broth. Presumably, the peptone and yeast extract in the Lauria broth contain trace metals that generate MDH activity.

The enhancement in MDH activity with $Zn^{2+}$ salts can be seen in similarity of the MDH amino acid sequence to the amino acid sequence of the Populus tremuloides sinapyl alcohol dehydrogenase (SAD), a enzyme known to require $Zn^{2+}$.[40] The two enzymes show a 70% identical and 80% similar amino acids sequences. When aligned, the MDH appears to have a similar metal binding site to the SAD suggesting similar metal requirements. SAD can be used as a template for engineering the active site of MDH for modified properties, such as changes to substrate specificity.

Example 3

Temperature vs. Activity and Stability Studies

The recombinant MDH was tested for activity at various temperatures. Lysates containing expressed MDH were incubated with D-mannitol and NAD at pH 9.0. Activity was measured by measuring the increased NADH concentration spectrophotometrically at $A_{340nm}$. MDH showed maximal activity at approximately 39° C. See, FIG. 12.

The thermostability of recombinant MDH was also tested. Lysates containing MDH were incubated at various temperatures. Aliquots of MDH were removed at various times to measure MDH activity using the assay described above. See, FIG. 13.

Most MDH activity was lost after four hours of incubation, except at 25° C. The loss may be partially due to proteases present in the lysates. However, this experiment probably gives a good representation of the overall thermostability of the MDH considering the overall speed of the degradation. Purified MDH can be used to remove the potential for protease degradation.

Example 4

Assay Development for MDH Engineering

Figure 3:
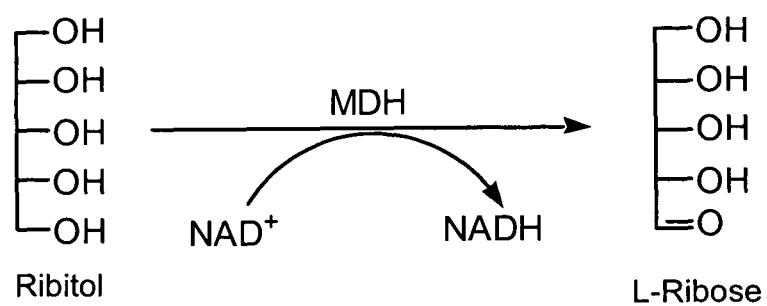
FIG. 3 shows a NADH-based high-throughput activity assay.

To improve the conversion rates of MDH with ribitol, assays were needed to identify those mutants with increased reaction rates for directed evolution experiments. High-throughput assays were designed that identify mutant MDH enzymes that display improved conversion of L-ribose from ribitol. See, FIG. 3. With this screen, increased NADH concentrations were measured spectrophotometrically as the L-ribose was being produced by MDH.

This screening method has been used successfully with other enzymes [22, 23] as well as offering enormous flexibility in testing reaction conditions. With this screen, several different reaction modifications can be monitored, such as activity at lower pH, improved thermostability, and modification of substrate specificity. A single MDH library can also be used against each of these modifications in parallel.

Figure 4:
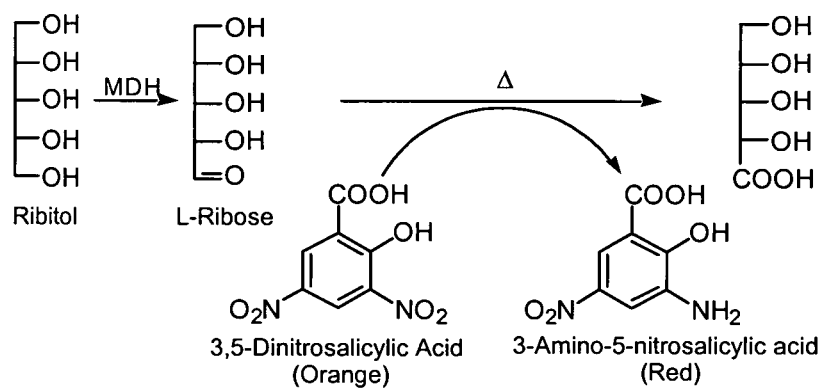
FIG. 4 shows a high-throughput reducing sugar assay to monitor increases in reaction rates for mutant MDH with ribitol.

The only major disadvantage of the NADH-based screen is that the assay does not look directly at product formation. A high-throughput reducing sugar assay can be used in order to directly measure the concentration of L-ribose synthesized. See, FIG. 4. Such assays have been described previously[24] and are commonly used, except in high-throughput. Such assay should work well in detecting the reaction productions of the oxidation of polyols to rare sugars. This assay is very powerful, because the assay can provide direct measurements of product formation instead of less reliable detection of secondary products or substrate loss. Initial tests are very encouraging as D-ribose and D-mannose samples gave significant color changes with this system while the ribitol and D-mannitol showed no color change upon heating.

To provide an accurate reducing sugar assay, consistent heating of the samples is critical for the high-throughput screen. All of the wells in the assay must be heated identically. This assay shows great potential in directly assessing product formation. While adding the high-throughput reducing sugar assay would improve the assay, this addition is not necessary for modifying and improving the synthetic potential of MDH. The NADH-based assay will provide an accurate, simple, and flexible high-throughput assay.

Example 5

Fermentation of Ribitol to L-Ribose

Because of the successes with the expression of MDH in *E. coli*, additional experiments were performed to determine the feasibility of the MDH system to produce L-ribose with MDH enzyme. Initial fermentation experiments were performed in shake-flasks using rich media and varying concentrations of ribitol. With 2% ribitol (w/v), the MDH-expressing strain converted approximately 25% of the ribitol to L-ribose with 48 hrs. The goal for this strain would be to have >90% conversion within 24-48 hrs.

Figure 5:
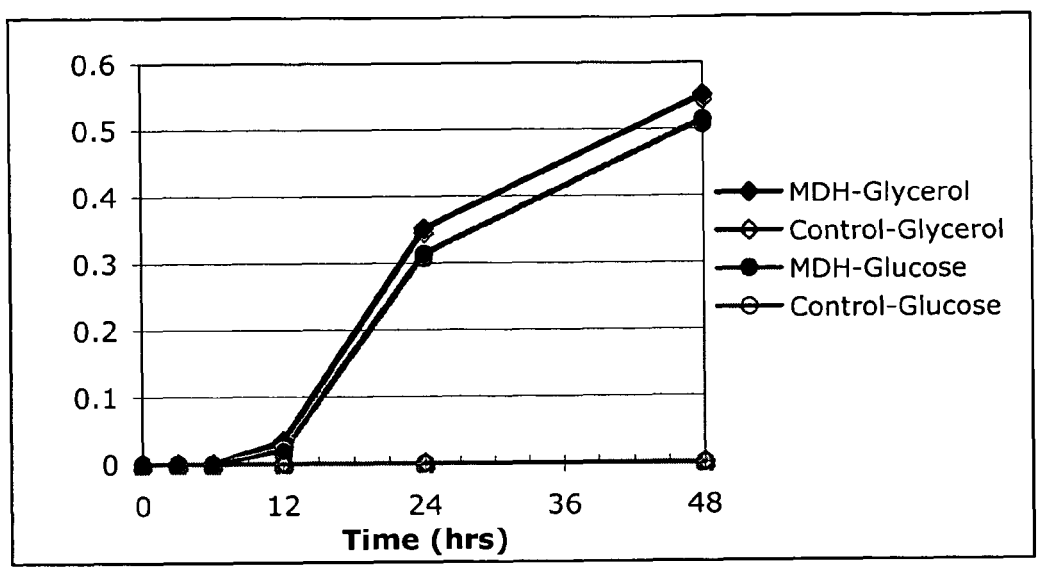
FIG. 5 shows comparison of MDH fermentation productivity using glycerol and glucose. All fermentations started with 2% (w/v) ribitol. Control reactions contained no mdh gene in the expression plasmid.
Figure 6A:
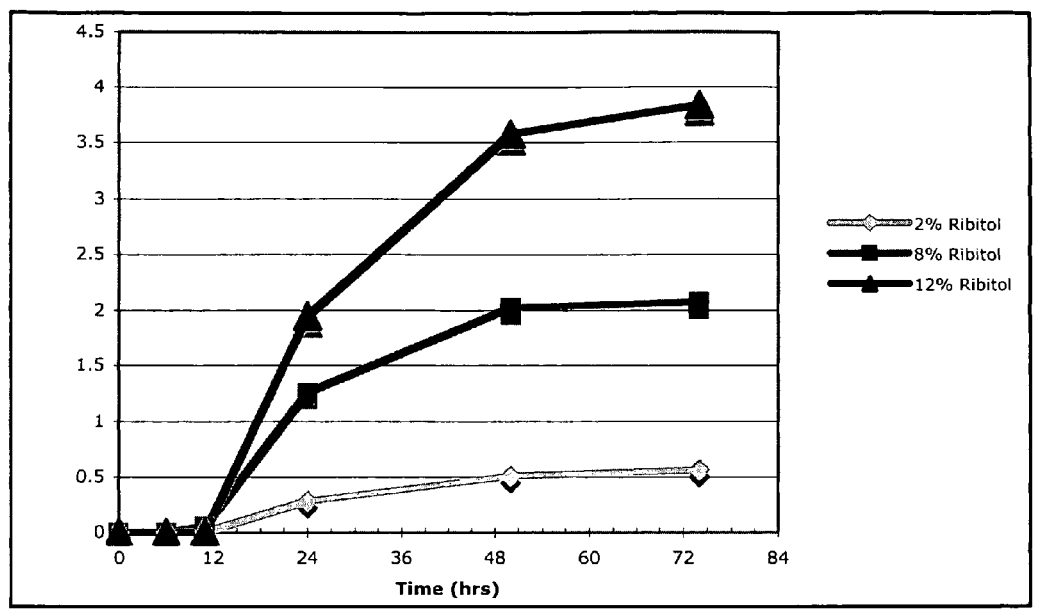
FIG. 6A-B: Comparison of MDH fermentation data using various initial concentrations of ribitol.
Figure 6B:
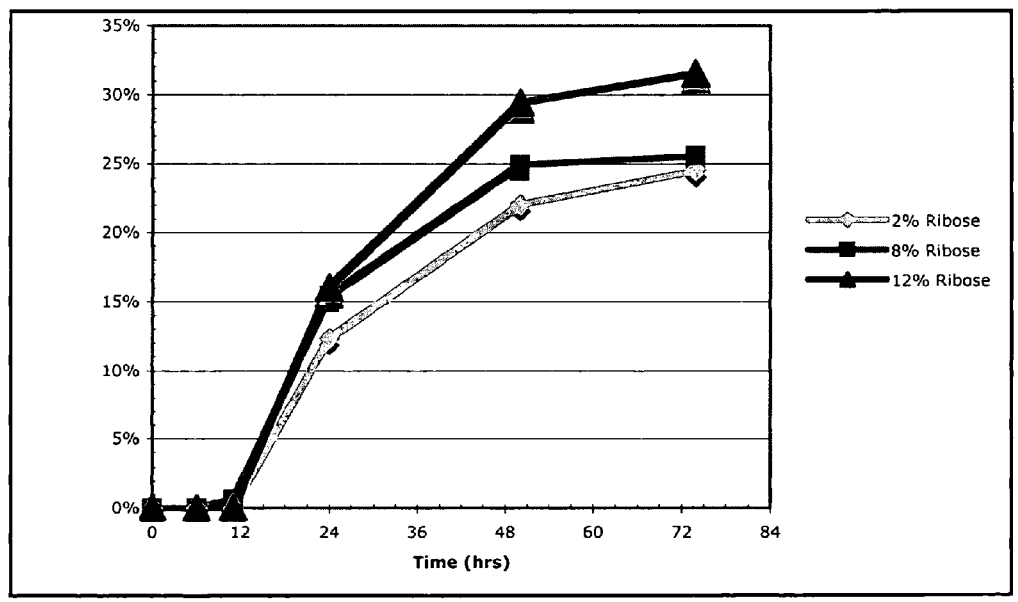

Further MDH fermentation experiments showed no difference in productivity when either glycerol or glucose was added as a carbon source in the media. See, FIG. 5. These results suggest that ribitol transport is not actively transported by a protein, because the presence of glucose in the media would have most likely suppressed the expression of such system.[26] Increasing the initial ribitol concentrations increased productivities and increased conversion rates. See, FIG. 6A-B.

The expression plasmid for MDH was also changed in an attempt to improve the L-ribose production. MDH was expressed in the pTRP338 plasmid. This low-copy uses a constitutive promoter and a kanamycin resistance gene. Comparative fermentation experiments were between the pTTQ18 and pTRP338 plasmids expressing MDH.

Figure 7:
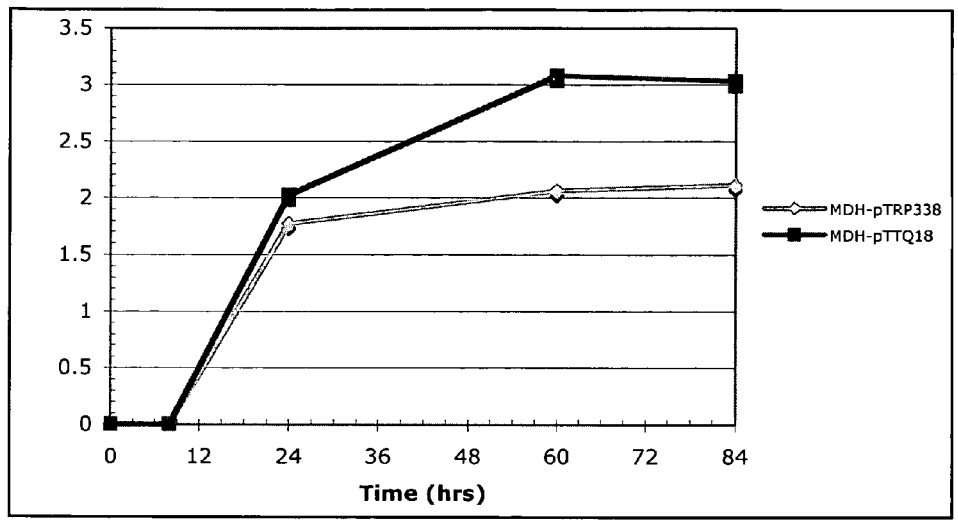
FIG. 7 shows comparison of expression plasmids on MDH fermentation productivity. Both fermentations used 11% (w/v) ribitol initially.

The pTTQ18 expression plasmid showed better fermentation productivity. See, FIG. 7. The best attributes of each expression plasmid will be combined to optimize the L-ribose production. Ultimately, the system will be incorporated into the genome of the production strain to relieve the burden of plasmid maintenance.

Example 6

Bioconversion of D-Mannitol to D-Mannose

MDH shows significant potential to synthesize many different rare carbohydrates from inexpensive and readily available polyols. While fermentation worked well for producing L-ribose, not all of these potential rare sugars will be amenable to fermentation. One of these substrates is D-mannose from D-mannitol. *E. coli* K12 strains can ferment D-mannitol. While using a single carbohydrate in the fermentation for both a carbon source and enzyme substrate can be advantageous, the mannitol is phosphorylated while being transported into the cell resulting in a substrate unable to be used by MDH. As such, an in vitro bioconversion will be preferred. A bioconversion also provides added flexibility of starting material.

Figure 8:
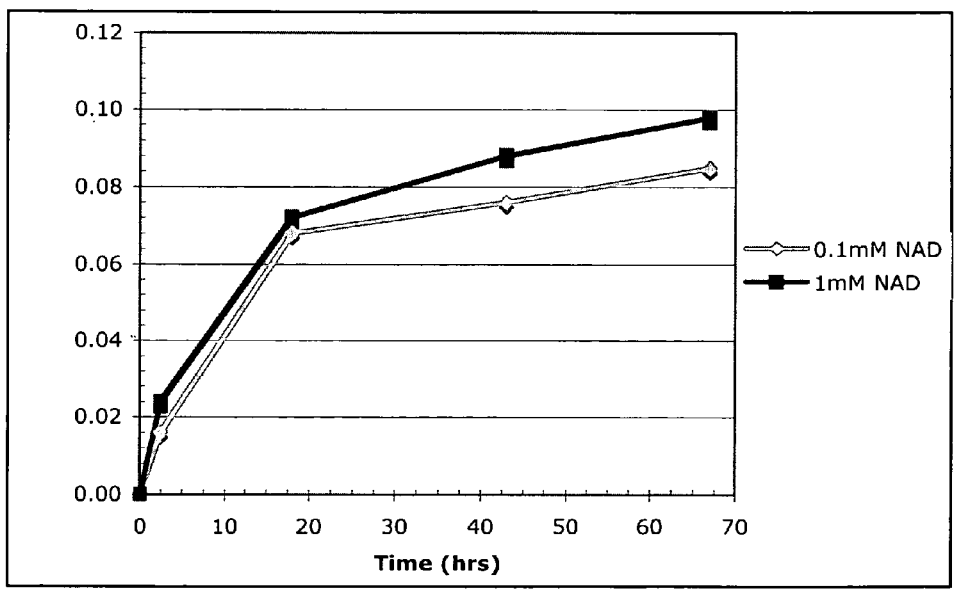
FIG. 8 shows effect of initial $NAD^+$ cofactor concentration on D-mannitol to D-mannose bioconversion using the MDH system.
Figure 9:
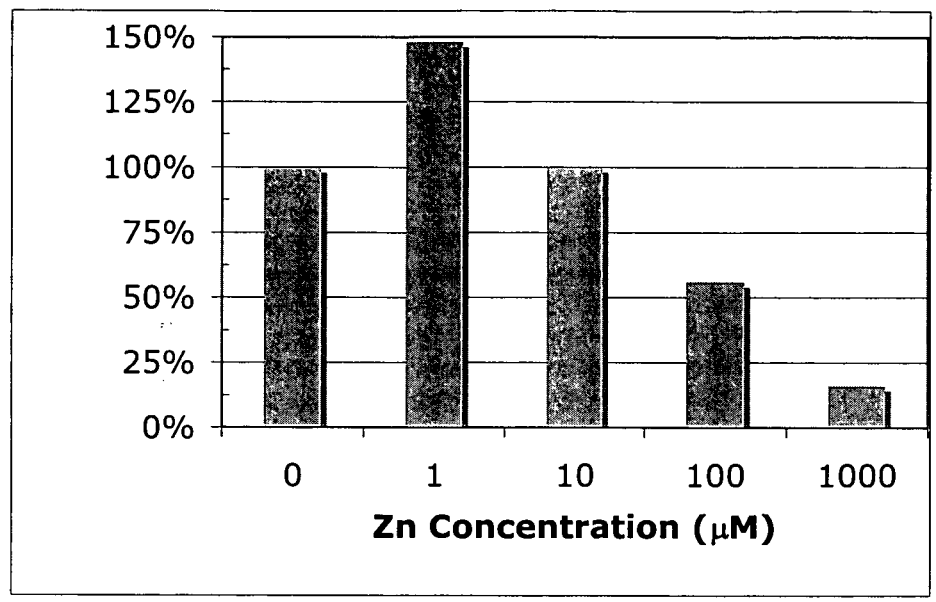
FIG. 9 shows MDH activity with increasing concentrations of $ZnSO_4$ in the presence of D-mannitol and NAD cofactor at pH 9.0.
Figure 10:
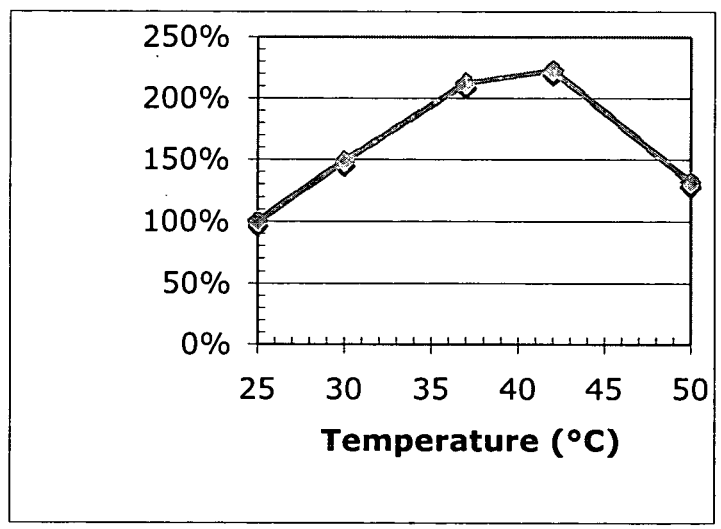
FIG. 10 shows MDH activity at various temperatures. Lysates containing expressed MDH were incubated with D-mannitol and NAD at pH 9.0.
Figure 11:
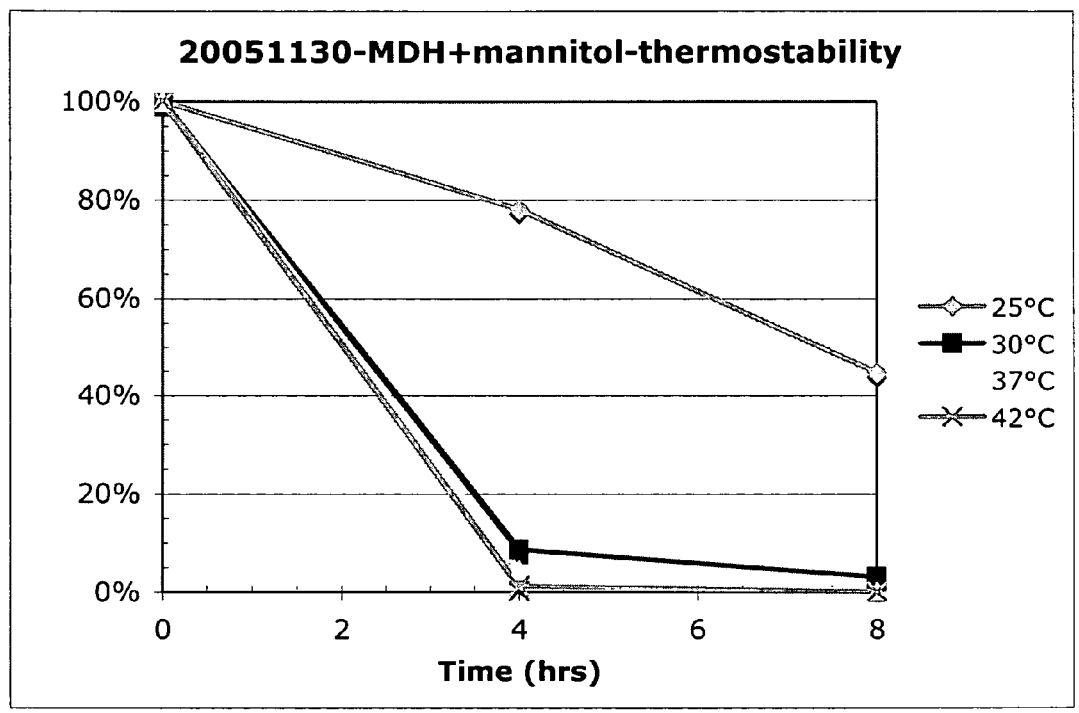
FIG. 11 shows a thermostability test of MDH.

The major disadvantage for bioconversions of oxidative reactions is the need to regenerate the NAD cofactor.[27] One such system tested was using pyruvate and L-lactic dehydrogenase (LDH).[27] Purified, recombinant MDH was tested with the LDH recycling system at 25° C., pH 9.0, and 100 mM starting D-mannitol and sodium pyruvate. Two different initial NAD cofactor concentrations were used to test the efficiency of cofactor recycling. See, FIG. 8.

Both reactions showed the production of D-mannose in excess of NAD cofactor, suggesting that cofactor recycling was occurring. Since the reaction rate was independent of NAD concentration, the limiting step was probably the MDH and not the cofactor recycling. While not an idealized system, this experiment shows the potential of the MDH system to produce many different rare sugars through a bioconversion process.

Several different strategies can be used to improve this bioconversion. First, over expression and activity of MDH can be improved by using directed evolution and protein engineering. By improving MDH, reactor productivity will be increased and ultimately reduce costs. The substrate specificity of MDH will be modified to include substrates used by the wild-type enzyme. Finally, an NADH oxidase can be used as a cofactor recycling system. Such systems utilize $O_2$ as the oxidant,[28] an advantageous factor over other systems like the LDH during carbohydrate purification. The Bommarius group at the Georgia Institute of Technology have NADH oxidase systems. These systems have proven useful in other bioconversions and can be used with MDH.[28, 29] An MDH system shows great potential and flexibility in producing L-ribose and other rare sugars for biochemical and pharmaceutical research.

Example 7

Substrate Specificity

The reaction rate of L-fucitol for recombinant MDH was tested. The relative reaction rate of L-fucitol was 10.5% the rate of D-mannitol. The fucitol was not originally characterized in the previous literature on MDH.[38] The inclusion of fucitol as a substrate for MDH suggests that carbohydrate derivatives can be used with this enzyme.

Example 8

The goals of the following experiments were to improve and expand the synthetic applications of the MDH system. These experiments include the scale-up and optimization of the L-ribose synthesis as well as the synthetic scale-up of other rare sugars relevant to biochemical and pharmaceutical research.

Improve the Expression and Activity of Mannitol Dehydrogenase.

The MDH system showed tremendous potential for the low-cost fermentation production of L-ribose from ribitol. However, the expression and activity of MDH can be improved. MDH does not over-express well in the *E. coli* expression strain. We estimate that less than 5% of the total soluble protein is MDH. If the expression of MDH can be increased several fold, the productivity of the fermentation strain should be increased. One option to increase the expression of the MDH is to change the expression plasmid and promoter. A high-copy plasmid with an inducible promoter has been used to express MDH. Other expression plasmids, including plasmids with medium and low-copy numbers as well as constitutive or temperature-induced promoters can be used. Other modifications to the expression plasmids, such as the distance from the ribosome-binding site and start codon for the mdh gene can be used to improve the expression of the MDH.

Increasing the activity of MDH can also be examined. One such method to increase activity is to increase MDH activity at neutral pH range. Currently, MDH has maximum activity of at pH 9.0 and only 10% residual activity at pH 7.0. By increasing the activity of MDH at neutral pH, MDH will have higher activity with an *E. coli* cell. A directed evolution approach can be used to modify these properties of MDH. The thermostability of MDH can also be improved. Expression at 30° C. gives the greatest expression of active MDH. By improving the thermostability of MDH, the fermentation can be run at 37° C. thus allowing faster *E. coli* growth and improved fermentation productivity. The same assays described above can also be used for these screens. The NADH-linked activity assay provides significant flexibility to test MDH activity for improvement of many different properties. By screening a sufficiently large and diverse MDH mutant library, mutations will be found that will improve MDH expression and activity and therefore lower the production costs for L-ribose and the many other rare sugars synthetically accessible with the MDH system.

Scale-Up of L-Ribose Fermentation.

Both productivity rates and conversion efficiencies can be improved as well as scale-up of MDH fermentation to provide an inexpensive source of L-ribose. The scale-up experiments include testing improved MDH enzymes derived above, improving the *E. coli* fermentation strain to improve productivity, and optimizing L-ribose recovery and purification.

One goal for the fermentation would be the synthesis of 100-150 g·L$^{-1}$ of L-ribose in 24-48 hrs with >90% conversion efficiency from ribitol. Initial fermentation results with the wild-type MDH show a productivity of approximately 35 g·L$^{-1}$ in 48 hrs with 30% ribitol converted. This result is very promising because this uses the wild-type MDH and an unoptimized *E. coli* strain.

To optimize the fermentation conditions, 14 stirred-tank fermenters (B. Braun Biostat B) can be used for 1 L fermentation development experiments as well as two 30 L and two 100 L fermenters for scale-up studies. Conditions are generally well known for high-density aerobic cultivation of *E. coli*.[30, 31] However, specific conditions for optimal production of L-ribose by production organisms can be determined by one of skill in the art. Initial experiments can focus on basic growth parameters such as temperature, pH and medium components. Optimized nitrogen and carbon feeding protocols and aeration rates can then be established. Fractional factorial designs are readily available for these types of experiments and can be applied as needed.[32] The equipment to test continuous cell-recycle reactor processes is known.[33] In the event that the engineering of the production strain for L-ribose production results in undesirable fermentation properties, directed evolution and continuous culture techniques[34] can be applied to overcome these problems.

Our previous fermentation results suggest that ribitol is transported passively through the membrane for the conversion of ribitol into L-ribose. We have investigated the coexpression of ribitol transport proteins in the fermentation strain. Ribitol transport proteins (rbT) have been characterized in both *E. coli* B-strains and *Klebsiella pnuemonae*.[35, 41, 42] These proteins have been cloned and recombinantly expressed in *E. coli*. Experiments with the *E. coli* rbT showed lower conversion rates of ribitol to L-ribose than fermentation strains not coexpressing the rbT. rbT expression can be optimized to provide an improved rate of L-ribose production. We have also expressed *Klebsiella* rbT. We have shown improvements in polyol production by coexpressing rbT.

Testing and Scale-Up In Vitro Bioconversion and/or Fermentation of Other Rare Sugars.

One of the true strengths of the MDH system is the flexibility in substrate specificity to synthesize many, different rare sugars from inexpensive and readily available starting materials.[16] By researching the synthesis of L-ribose an enabling synthetic strategy has been created for creating rare sugars.

Two general techniques can be used for producing rare sugars: fermentation and in vitro bioconversion. Each technique has advantages and disadvantages for each rare sugar. Fermentations offer in vivo cofactor recycling and ease of scale for large quantities, but offer additional challenges of added purification requirements and problems if the carbohydrate or polyol is metabolized by the fermentation strain. The bioconversion offers ease of purification and lack of side products, but requires cofactor recycling and scale-up issues.

The first rare sugar is D-mannitol from D-mannitol. D-mannose demand is increasing with its increasing use in the production of pharmaceuticals.[11] MDH systems can help meet this demand by providing an inexpensive source of D-mannose.

Above, we used MDH to synthesize D-mannose from D-mannitol through a bioconversion with cofactor recycling. This initial reaction showed the feasibility of MDH for a bioconversion. Fermentation and bioconversion can be tested to determine which will be more suitable for producing large quantities of D-mannose. While the bioconversion offers ease of purification, the fermentation route offers scalability. Because of these scalability concerns, fermentation may be the favorable route. One potential obstacle in using D-mannitol with fermentation is that *E. coli* metabolizes both D-mannitol and D-mannose.[21] D-Mannitol may be used as a sole carbon-source to provide both a fermentable carbon source and the starting material for MDH, the D-mannitol is phosphorylated to mannitol-1-phosphate during active transport thus rendering the mannitol synthetically accessible to MDH. As such, both the mannitol and mannose metabolic pathways will need to be deleted, thus requiring another carbon-source for metabolism, such as glucose. Engineering *E. coli* strains for fermentation processes is well known and production of a commercially viable strain to synthesize large quantities of D-mannose is within skill of the art.

While D-mannose will require the development of a fermentation strain to create large-scale quantities, other rare sugars may not require such large-scale production to meet the needs of discovery medicinal chemistry and biochemical research. One such rare sugar is L-gulose. L-gulose is produced during the de novo synthesis of L-ascorbic acid in plants, and therefore, small scales may be needed in biochemical research.[36] MDH can synthesize L-gulose from D-sorbitol. Given the current costs for obtaining L-gulose, demand for it will probably be small and only require small pilot scales to meet initial demand. As such, a bioconversion may be adequate instead of the development of a fermentation strain. A bioconversion could provide sufficient productivity and ease of purification. If demand increased, more research would be devoted to producing large-scale quantities of L-gulose either with a larger bioconversion or fermentation. These two examples illustrate the technical questions for producing large quantities of rare sugars. Each rare sugar will require simple bioprocess testing to determine the feasibility of each route. The MDH system provides a platform technology to meet the demands of pharmaceutical and biochemical researchers for rare sugars that are not being met by current fine chemical processes.

Example 9

Optimize the NADH Oxidase for Cofactor Recycling

Not every rare sugar synthetically accessible with MDH will be amenable to fermentation. Therefore, an efficient NAD-cofactor recycling method will be needed. One such technology for this cofactor recycling is with NADH oxidases (NOX, E.C. 1.6.-.-.).[28] These oxidases utilize $O_2$ to convert NADH to NAD and generate $H_2O$ or $H_2O_2$. Water forming NOX enzymes would offer distinct advantages over other cofactor recycling methods because of the low costs of substrate ($O_2$) and lack of additional purification of end products.

The Bommarius group has isolated a water-forming NOX from *Lactobacillus sanfranciscensis*.[28] This NOX accepts both NADH and NADPH cofactors and has been successfully used by the Bommarius group in the preparation of chiral compounds.[29] This NOX can be recombinantly expressed in *E. coli* and displays high specific activity (221 units/mg). By including DTT into the reaction media, the total turnover number for the NOX is 112,500 at pH 7.0.[29] The addition of DTT is advantageous since MDH activity is enhanced in the presence of DTT. Assuming a typical cost of NAD is $10 per gram, this turnover number for NOX would result in approximately $0.06 in cofactor costs per mole of product or approximately $0.40 in cofactor costs per kilogram of rare sugar.[29] This NOX technology will provide a significant costs savings with both cofactor recycling and purification.

This NOX technology provides a significant platform for creating cost-effective bioconversions of many rare sugars. NOX for the MDH system can be fully optimized. The activity and pH profile of NOX using directed evolution technologies can be improved. The pH optimum for the NOX is 7.0.[28] Protein engineering and directed evolution efforts can be used to increase the activity of the NOX at a pH range. This effort combined with directed evolution experiments described above to improve MDH thermostability and activity at neutral pH ranges should provide a excellent technology to synthesize a broad range of rare sugars for the pharmaceutical and biochemical research.

CONCLUSION

MDH systems show great promise in the production of L-ribose and other rare sugars from inexpensive and readily available starting materials. Experiments demonstrate that MDH systems display a high level of both productivity as well as flexibility in the substrate specificity. An optimized MDH can be created for a cost-effective bioprocess for L-ribose. MDH systems can then be extended to other rare sugars. These processes provide an inexpensive and readily available source to reduce the costs of synthesizing pharmaceuticals as well as provide access to new synthetic targets for medicinal and biochemical researchers to create improved medicines.

REFERENCES CITED

1. Ahmed, Z., *Production of Natural and Rare Pentoses Using Microorganisms and Their Enzymes*. Electronic Journal of Biotechnology, 2001. 4(2): p. 103-11.
2. Allen, J. R., C. R. Harris, and S. J. Danishefsky, *Pursuit of optimal carbohydrate-based anticancer vaccines: Preparation of a multiantigenic unimolecular glycopeptide containing the Tn, MBr1, and Lewis(y) antigens*. Journal of the American Chemical Society, 2001. 123(9): p. 1890-1897.
3. Bartolozzi, A. and P. H. Seeberger, *New approaches to the chemical synthesis of bioactive oligosaccharides*. Current Opinion in Structural Biology, 2001. 11(5): p. 587-592.
4. Koeller, K. M. and C. H. Wong, *Emerging themes in medicinal glycoscience*. Nature Biotechnology, 2000. 18(8): p. 835-841.
5. Wang, P., et al., *Recent advances in L-nucleosides: chemistry and biology*. Antiviral Res, 1998. 40(1-2): p. 19-44.
6. Gumina, G., G. Y. Song, and C. K. Chu, *L-Nucleosides as chemotherapeutic agents*. FEMS Microbiol Lett, 2001. 202(1): p. 9-15.
7. Casey, J. L., et al., *Method of Treating Hepatitis Delta Virus Infection*. 2003, Georgetown University, Cornell Research Foundation, Inc., University of Georgia Research Foundation, Inc.: United States of America.
8. Doong, S. L., et al., *Inhibition of the replication of hepatitis B virus in vitro by 2',3'-dideoxy-3'-thiacytidine and related analogues*. Proc Natl Acad Sci USA, 1991. 88(19): p. 8495-9.
9. Ramaasamy, K., R. Tam, and D. Averett, *Monocyclic L-Nucleosides, Analogs and Uses Thereof* 2003, ICN Pharmaceuticals, Inc.: United States of America.

10. Du, J., et al., *A practical synthesis of L-FMAU from L-arabinose*. Nucleosides Nucleotides, 1999. 18(2): p. 187-95.
11. Rouhi, A. M., *Chiral Business, in Chemical and Engineering News*. 2004. p. 45-61.
12. Thorre, D. V., *Process For Obtaining Bio-Functional Fractions From Biomass*. 2003, BioRefining, Inc.: United States of America.
13. Jokela, J., O. Pastinen, and M. Leisola, *Isomerization of Pentose and Hexose Sugars by an Enzyme Reactor Packed with Cross-Linked Xylose Isomerase Crystals*. Enzyme and Microbial Technology, 2002. 31: p. 67-76.
14. Seo, M. J., et al., *One-Pot Inversion of D-Mannono-1,4-Lactone For the Practical Synthesis of L-Ribose*. Tetrahedron Letters, 2003. 44: p. 3051-2.
15. Kawaguchi, T., M. Hara, and M. Ueda, *Process For Producing L-Ribose*. 2002, Mitsubishi Chemical Corp.: United States of America.
16. Stoop, J. M., W. S. Chilton, and D. M. Pharr, *Substrate Specificity of the NAD-Dependent Mannitol Dehydrogenase From Celery*. Phytochemistry, 1996. 43(6): p. 1145-50.
17. Stoop, J. M., et al., *Purification of NAD-dependent mannitol dehydrogenase from celery suspension cultures*. Plant Physiol, 1995. 108(3): p. 1219-25.
18. Williamson, J. D., et al., *Sequence analysis of a mannitol dehydrogenase cDNA from plants reveals a function for the pathogenesis-related protein ELI3*. Proc Natl Acad Sci USA, 1995. 92(16): p. 7148-52.
19. Schallmey, M., A. Singh, and O. P. Ward, *Developments in the use of Bacillus species for industrial production*. Can J Microbiol, 2004. 50(1): p. 1-17.
20. Wright, J. V. and L. Lenard, *The Natural Alternative to Antibiotics*. 2001: Dragon Art.
21. *Escherichia Coli and Salmonella*. 2nd Edition ed, ed. F. C. Neidhardt and R. Curtiss. 1996: ASM Press. 2822.
22. Bloom, J. D., et al., *Evolving Strategies for Enzyme Engineering*. Current Opinion in Structural Biology, 2005. 15: p. 447-52.
23. Yano, Y., S. Oue, and H. Kagamiyama, *Directed Evolution of an Aspartate Aminotransferase With New Substrate Specificities*. Proc Natl Acad Sci USA, 1998. 95: p. 5511-5.
24. Yang, J., et al., *Studies on the substrate specificity of Escherichia coli galactokinase*. Org Lett, 2003. 5(13): p. 2223-6.
25. Osepchuk, J. M., *A History of Microwave Heating Applications*. IEEE Transactions on Microwave Theory and Techniques, 1984. 32(9): p. 1200-24.
26. Nichols, N. N., B. S. Dien, and R. J. Bothast, *Use of Catabolite Repression Mutants for Fermentation of Sugar Mixtures of Ethanol*. Applied Microbiology and Biotechnology, 2001.56: p. 120-5.
27. Kroutil, W., et al., *Biocatalytic Oxidation of Primary and Secondary Alcohols*. Advanced Synthesis and Catalysis, 2004. 346(2-3): p. 125-42.
28. Riebel, B. R., et al., *Cofactor Regeneration of both NAD from NADH and NADP from NADPH: NADH Oxidase from Lactobacillus sanfranciscensis*. Advanced Synthesis and Catalysis, 2003. 245: p. 707-12.
29. Odman, P., W. B. Wellborn, and A. S. Bommarius, *An Enzymatic Process to α-Ketoglutarate from L-Glutamate: The Coupled System L-Glutamate Dehydrogenase/NADH Oxidase*. Tetrahedron: Asymmetry, 2004. 15: p. 2933-37.
30. Lee, S. Y., *High Cell Density Culture of Escherichia coli*. Trends in Biotechnology, 1996. 14: p. 98-105.
31. Riesenberg, D. and R. Guthke, *High Cell Density Cultivation of Microorganisms*. Applied Microbiology and Biotechnology, 1999. 51: p. 422-30.
32. Strobel, R. J. and G. R. Sullivan, *Experimental Design for Improvement of Fermentations*. Manual of Industrial Microbiology and Biotechnology, ed. A. L. Demain and J. E. Davies. 1999, Washington, D.C.: ASM Press.
33. Chang, H. N., I.-K. Yoo, and B. S. Kim, *High Density Cell Culture by Membrane-Based Cell Recycle*. Biotechnology Advances, 1994. 12: p. 467-87.
34. Zelder, O. and B. Hauer, *Environmentally Directed Mutations and Their Impact on Industrial Biotransformation and Fermentation Processes*. Current Opinion in Microbiology, 2000. 3: p. 248-51.
35. Reiner, A. M., *Genes for Ribitol and D-Arabitol Catabolism in Escherichia coli: Their Loci in C Strain and Absence in K-12 and B Strains*. Journal of Bacteriology, 1975. 123(2): p. 530-6.
36. Wolucka, B. A. and M. Van Montagu, *GDP-Mannose-3', 5'-Epimerase Forms GDP-L-Gulose, a Putative Intermediate for the de novo Biosynthesis of Vitamin C in Plants*. Journal of Biological Chemistry, 2003(278): p. 48.
37. Stoop, J. M., et al., *Purification of NAD-dependent mannitol dehydrogenase from celery suspension cultures*. Plant Physiol, 1995. 108(3): p. 1219-25.
38. Stoop, J. M., W. S. Chilton, and D. M. Pharr, *Substrate Specificity of the NAD-Dependent Mannitol Dehydrogenase From Celery*. Phytochemistry, 1996. 43(6): p. 1145-50.
39. Williamson, J. D., et al., *Sequence analysis of a mannitol dehydrogenase cDNA from plants reveals a function for the pathogenesis-related protein ELI3*. Proc Natl Acad Sci USA, 1995. 92(16): p. 7148-52.
40. Bomati, E. K. and J. P. Noel, *Structural and kinetic basis for substrate selectivity in Populus tremuloides sinapyl alcohol dehydrogenase*. Plant Cell, 2005. 17(5): p. 1598-611.
41. Reiner, A. M., *Genes for Ribitol and D-Arabitol Catabolism in Escherichia coli: Their Loci in C Strain and Absence in K-12 and B Strains*. Journal of Bacteriology, 1975. 123(2): p. 530-6.
42. Heuel, H., et al., *Genes for D-arabinitol and ribitol catabolism from Klebsiella pneumoniae*. Microbiology, 1998.144 (Pt 6): p. 1631-9.

We claim:

1. A method for producing L-ribose comprising fermenting a substrate comprising ribitol with one or more recombinant bacteria or yeast that expresses a recombinant *Apium graveolens* mannitol-1-dehydrogenase (MDH), wherein (1) the recombinant *Apium graveolens* MDH has a greater reaction rate than native MDH or (2) the one or more recombinant bacteria or yeast convert approximately 25% of ribitol to L-ribose within 48 hours, whereby L-ribose is produced.

2. The method of claim 1, wherein the recombinant *Apium graveolens* mannitol-1-dehydrogenase (MDH) is encoded by a nucleic acid molecule comprising SEQ ID NO:1.

3. The method of claim 1, wherein the recombinant *Apium graveolens* mannitol-1-dehydrogenase (MDH) comprises SEQ ID NO:2.

4. The method of claim 1, wherein the one or more recombinant bacteria or yeast express ribitol transport proteins (rbT).

5. The method of claim 1, wherein the substrate is further contacted with a NADH oxidase.

6. The method of claim 5, wherein the NADH oxidase is NOX from *Lactobacillus sanfranciscensis*.

7. A method for producing L-ribose from a substrate comprising D-ribose comprising:
   (a) converting D-ribose to ribitol; and
   (b) fermenting the ribitol with one or more recombinant bacteria or yeast that express a recombinant *Apium graveolens* mannitol-1-dehydrogenase (MDH), wherein (1) the recombinant *Apium graveolens* MDH has a greater reaction rate than native MDH or (2) the one or more recombinant bacteria or yeast convert approximately 25% of ribitol to L-ribose within 48 hours, whereby L-ribose is produced.

8. The method of claim 7, wherein the recombinant *Apium graveolens* mannitol-1-dehydrogenase (MDH) is encoded by a nucleic acid molecule comprising SEQ ID NO:1.

9. The method of claim 7, wherein the recombinant *Apium graveolens* mannitol-1-dehydrogenase (MDH) comprises SEQ ID NO:2.

10. The method of claim 7, wherein the one or more recombinant bacteria or yeast express ribitol transport proteins (rbT).

11. The method of claim 7, wherein the ribitol is further contacted with a NADH oxidase.

12. The method of claim 11, wherein the NADH oxidase is NOX from *Lactobacillus sanfranciscensis*.

13. The method of claim 7, wherein the D-ribose is converted to ribitol by chemical reduction.

14. The method of claim 7, wherein D-ribose is converted to ribitol by fermentation.

15. A method for producing a sugar from a substrate comprising fermenting the substrate with one or more recombinant bacteria or yeast that express a recombinant *Apium graveolens* mannitol-1-dehydrogenase (MDH), wherein the recombinant *Apium graveolens* MDH has a greater reaction rate than native MDH, whereby the sugar is produced, wherein the sugar is D-arabanose and the substrate is D-arabitol; wherein the sugar is L-erythrose and the substrate is erythritol; wherein the sugar is L-gulose and the substrate is L-sorbitol; wherein the sugar is L-galactose and the substrate is i-galactitol; wherein the sugar is D-threose and the substrate is D-threitol; wherein the sugar is L-fucose and the substrate is L-fucitol; or wherein the sugar is D-lyxose and the substrate is D-arabitol.

16. The method of claim 15, wherein the recombinant *Apium graveolens* mannitol-1-dehydrogenase (MDH) is encoded by a nucleic acid molecule comprising SEQ ID NO:1.

17. The method of claim 15, wherein the recombinant *Apium graveolens* mannitol-1-dehydrogenase (MDH) comprises SEQ ID NO:2.

18. The method of claim 15, wherein the one or more recombinant bacteria or yeast express ribitol transport proteins (rbT).

19. The method of claim 15, wherein the recombinant *Apium graveolens* mannitol-1-dehydrogenase (MDH) is encoded by a nucleic acid molecule having optimized codon usage for the one or more recombinant bacteria or yeast used for expression of the *Apium graveolens* mannitol-1-dehydrogenase (MDH).

20. The method of claim 15, wherein the substrate is further contacted with a NADH oxidase.

21. The method of claim 20, wherein NADH oxidase is NOX from *Lactobacillus sanfranciscensis*.

22. A method for producing D-mannose comprising fermenting a substrate comprising D-mannitol with one or more recombinant bacteria or yeast that express a recombinant *Apium graveolens* mannitol-1-dehydrogenase (MDH), wherein the recombinant *Apium graveolens* MDH has a greater reaction rate than native MDH, and contacting the substrate with a NADH oxidase, whereby D-mannose is produced.

23. The method of claim 22, wherein the recombinant *Apium graveolens* mannitol-1-dehydrogenase (MDH) comprises SEQ ID NO:2 and the NADH oxidase is NOX from *Lactobacillus sanfranciscensis*.

* * * * *

SEQUENCE LISTING

<160> NUMBER OF SEQ ID NOS: 2

<210> SEQ ID NO 1
<211> LENGTH: 1098
<212> TYPE: DNA
<213> ORGANISM: Apium graveolens

<400> SEQUENCE: 1

```
atggcgaaaa gcagcgaaat cgaacacccg gtgaaagcgt ttggttgggc ggcacgtgat      60
accaccggtc tgctgagccc gttcaaattt agccgtcgcg cgaccggcga aaaagatgtg     120
cgcctgaaag tgctgtttag cggcgtgtgc cacagcgatc accacatgat ccacaacaac     180
tggggcttca ccacctatcc gatcgtgccg ggccatgaaa ttgtgggcgt ggtgaccgaa     240
gtgggcagca agtggaaaaa agtgaaagtg ggcgataacg tgggcattgg ctgcctggtt     300
ggtagctgcc gtagctgcga aagctgctgc gataaccgcg aaagccactg cgaaaacatc     360
atcgatacct acggcagcat ctacttcgat ggcaccatga cccatggcgg ctacagcgat     420
accatggtgg cggatgaaca cttcattctg cgctggccga aaaacctgcc gctggattct     480
ggtgcaccgc tgctgtgtgc gggcattacc acctacagcc cgctgaaata ctacggcctg     540
gataaaccgg gcaccaaaat cggtgtggtg ggcctgggtg gtctgggtca tgtggcggtg     600
aaaatggcga agcgttcgg tgcgcaggtg accgtgatcg atatcagcga agcaaacgc     660
aaagaagcgc tggaaaaact gggcgcggat agcttcctgc tgaacagcga tcaagaacag     720
atgaaaggcg cgcgtagcag cctggatggc attatcgata ccgtgccggt gaatcatccg     780
ctggcgccgc tgttcgatct gctgaaaccg aacggcaaac tggtgatggt tggtgcgccg     840
gaaaaaccgt tcgaactgcc ggtgttcagc ctgctgaaag gccgtaaact gctgggcggc     900
accattaacg gcggcatcaa agaaacccag gaaatgctgg atttcgcggc gaaacacaac     960
atcaccgcgg atgtggaagt gatcccgatg gattacgtga acaccgcgat ggaacgcctg    1020
gtgaaaagcg atgtgcgcta ccgcttcgtg attgatatcg cgaatacgat gcgtaccgaa    1080
gaaagcctgg cgcgcgtaa                                                 1098
```

<210> SEQ ID NO 2
<211> LENGTH: 365
<212> TYPE: PRT
<213> ORGANISM: Apium graveolens
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid

<400> SEQUENCE: 2

Met Ala Lys Ser Ser Glu Ile Glu His Pro Val Lys Ala Phe Gly Trp
1               5                   10                  15

Ala Ala Arg Asp Thr Thr Gly Leu Leu Ser Pro Phe Lys Phe Ser Arg
            20                  25                  30

Arg Ala Thr Gly Glu Lys Asp Val Arg Leu Lys Val Leu Phe Xaa Gly
        35                  40                  45

Val Cys His Ser Asp His His Met Ile His Asn Asn Trp Gly Phe Thr
    50                  55                  60

Thr Tyr Pro Ile Val Pro Gly His Glu Ile Val Gly Val Val Thr Glu
65                  70                  75                  80

Val Gly Ser Lys Val Glu Lys Val Lys Val Gly Asp Asn Val Gly Ile
                85                  90                  95

Gly Cys Leu Val Gly Ser Cys Arg Ser Cys Glu Ser Cys Cys Asp Asn
            100                 105                 110

Arg Glu Ser His Cys Glu Asn Xaa Ile Asp Thr Tyr Gly Ser Ile Tyr
        115                 120                 125

Phe Asp Gly Thr Met Thr His Gly Gly Tyr Ser Asp Thr Met Val Ala 130                 135                 140
Asp Glu His Phe Ile Leu Arg Trp Pro Lys Asn Leu Pro Leu Asp Ser
145                 150                 155                 160

Gly Ala Pro Leu Leu Cys Ala Gly Ile Thr Thr Tyr Ser Pro Leu Lys
            165                 170                 175

Tyr Tyr Gly Leu Asp Lys Pro Gly Thr Lys Ile Gly Val Val Gly Leu
            180                 185                 190

Gly Gly Leu Gly His Val Ala Val Lys Met Ala Lys Ala Phe Gly Ala
            195                 200                 205

Gln Val Thr Val Ile Asp Ile Ser Glu Ser Lys Arg Lys Glu Ala Leu
    210                 215                 220

Glu Lys Leu Gly Ala Asp Ser Phe Leu Leu Asn Ser Asp Gln Glu Gln
225                 230                 235                 240

Met Lys Gly Ala Arg Ser Ser Leu Asp Gly Ile Ile Asp Thr Val Pro
            245                 250                 255

Val Asn His Pro Leu Ala Pro Leu Phe Asp Leu Leu Lys Pro Asn Gly
            260                 265                 270

Lys Leu Val Met Val Gly Ala Pro Glu Lys Pro Phe Glu Leu Pro Val
            275                 280                 285

Phe Ser Leu Leu Lys Gly Arg Lys Leu Leu Gly Gly Thr Ile Asn Gly
    290                 295                 300

Gly Ile Lys Glu Thr Gln Glu Met Leu Asp Phe Ala Ala Lys His Asn
305                 310                 315                 320

Ile Thr Ala Asp Val Glu Val Ile Pro Met Asp Tyr Val Asn Thr Ala
            325                 330                 335

Met Glu Arg Leu Val Lys Ser Asp Val Arg Tyr Arg Phe Val Ile Asp
            340                 345                 350

Ile Ala Asn Thr Met Arg Thr Glu Glu Ser Leu Gly Ala
            355                 360                 365